United States Patent [19]
Chappell et al.

[11] 3,967,629
[45] July 6, 1976

[54] BICYCLIC FRAGRANCE MATERIALS AND PROCESSES THEREFOR

[75] Inventors: Robert L. Chappell, East Windsor, N.J.; Edward J. Shuster, Brooklyn, N.Y.; Joaquin F. Vinals, Red Bank; Manfred H. Vock, Locust, both of N.J.

[73] Assignee: International Flavors & Fragrances Inc., New York, N.Y.

[22] Filed: Oct. 1, 1973

[21] Appl. No.: 402,157

[52] U.S. Cl. .............................. 131/144; 131/17 R
[51] Int. Cl.² .................... A24B 13/00; A24B 15/04
[58] Field of Search .................... 131/2, 15, 17, 144, 131/17 R

[56] References Cited
UNITED STATES PATENTS 3,746,010   7/1973   Leffingwell .......................... 131/144
3,840,023   10/1974  Demole ................................ 131/144

Primary Examiner—Robert W. Michell
Assistant Examiner—V. Millin
Attorney, Agent, or Firm—Brooks Haidt Haffner & Delahunty

[57] ABSTRACT

The use of saturated and unsaturated polyalkyl bicyclo-[2.2.2]-octanes and/or alcohols and aldehydes thereof to alter organoleptic properties, and particularly the aroma, of consumable materials, together with compositions containing such bicyclic materials; and novel bicyclo-[2.2.2]-octane derivatives and processes for preparing them.

2 Claims, No Drawings

BICYCLIC FRAGRANCE MATERIALS AND PROCESSES THEREFOR

BACKGROUND OF THE INVENTION

The present invention relates to the use of certain bicyclic octane derivatives in altering organoleptic properties, such as flavors and aromas, and compositions suited to such uses, as well as to certain novel bicyclic octane derivatives and processes for preparing them.

A material having the structure

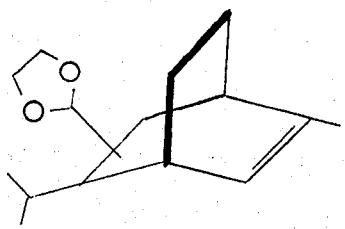

(dioxolane-substituted 5-isopropyl-7-methylbicyclo-[2.2.2]-oct-7-ene) has been sold by Societe Anonyme Des Establissements Roure Bertrand Fils Et Justin Dupont 17 Bis Rue Legendre Paris XVII$^e$ France under the name "Glycollierol" for use in perfumes. Dragoco, Gerberding & Co., GmbH, Holzminden, Federal Republic of Germany has sold a material having the structure

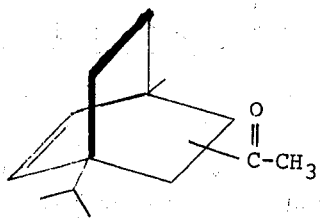

(carbomethoxy-substituted 1,4-dimethyl-bicyclo-[2.2.2]-oct-5-ene) as a perfume ingredient with a patchouli, vetivert type odor, under the name "Mahogonate".

U.S. Pat. No. 2,957,906 broadly shows acyl- and carboalkoxy-substituted bicyclooctene, among the other bicyclic compounds for pesticide and agricultural uses, and U.S. Pat. No. 3,304,167 shows various norbornane (bicyclo-[2.2.1]-heptane) derivatives, including nitrile derivatives and certain of the materials are said to be herbicidally active.

Danishevsky et al, Chem. Comm. 1968, 1287, show 1,3,3-trimethyl-6-isobutylbicyclo-[2.2.2]-octan-2-one and Kealy et al, J. Org. Chem., 26, 987 (1961) demonstrate 1,3-dimethyl-3-ethylbicyclo-[2.2.2]-octane and the corresponding bicyclooct-5-ene. Orahovats et al, Collect. Czech. Chem. Comm., 35(3), 838 (1970) show 2-hydroxy- and 2-oxo-substituted 3-methylbicyclo-[2.2.2]-oct-5-ene and the corresponding bicyclooctane. Organic Reactions, IV, 66 states that Diels and Alder, Ann. 478, 137 (1937) prepared bicyclo-[2.2.2]-oct-5-ene-8-carboxaldehyde and that α-phellandrene, 2-isopropyl-5-methylbicyclo-[2.2.2]-oct-5-en-7- and 8-carboxaldehyde were prepared by Diels and Alder, Ann. 470, 62 (1929).

Morita et al, J. Org. Chem. 30, 533 (1965, show various alkylated 4-alkoxybicyclo-[2.2.2]-octan-2-ones, and Curtin et al, J. Am. Chem. Soc. 81, 622 (1959) show methylated bicyclo-[2.2.2]-oct-5-en-2-ones. Various other bicyclo-[2.2.2]-octane materials and methods for their preparation are demonstrated by Petrov, J. Gen. Chem. U.S.S.R. 11, 809 (1941); Selca et al, Ber. 75, 1379 (1942); Kenyon and Young, J. Chem. Soc. 263 (1941); Alder et al, Ann. 543,1 (1939); Tich et al, Collect. Czech. Chem. Comm. 35(2), 459 (1970); Kraus et al, Ann. 708, 127 (1967); Berson et al, J. Am. Chem. Soc. 80, 5010 (1964); Karanskil et al, Zh. obshchei Khim. 29, 2976; McDonald et al, J. Org. Chem. 35, 1250 (1970); Curtin et al, J. Am. Chem. Soc. 81, 662 (1959); Conroy et al, J. Am. Chem. Soc. 75, 2530 (1953) and 78, 2290 (1957); Curtin et al, J. Am. Chem. Soc. 79, 3156 (1957); Waring et al, J. Am. Chem. Soc. 86, 1454 (1964); Alder et al, Ber. 90, 1709 (1957); Cookson et al, J. Chem. Soc. 2302 (1956); Kamamato, Chem. Abst. 58, 2391f (1963); and Cimarusti et al, J. Am. Chem. Soc. 90, 113 (1968).

German Offenlegungsschrift 2,242,913 shows tricyclic alcohol, denominated "nordehydro-patchoulol", extracted from patchouli alcohol. Tricyclic compounds have also been prepared by Greuber et al, Helv. Chim. Acta 55, 526 (1972). Various preparative procedures for preparation of tricyclic materials are exhibited by Waring et al, J. Am. Chem. Soc. 86, 1454 (1964) and Blum et al, Synthesis No. 4, 195 (1972). Quinones and quinols have been prepared by Chambers et al, J. Chem. Soc. (London) 1804 (1959) and McClure, J. Org. Chem. 28, 69 (1963). Various cyclic derivatives are demonstrated by Alder et al, Ber. 90, 1709 (1957) and Day, Chem. Rev. 53, 167 (1953).

THE INVENTION

Briefly, the present invention involves the use of certain alkylated saturated and unsaturated derivatives of bicyclo-[2.2.2]-octane, as well as certain novel derivatives and processes for preparing them. The compounds for use in altering the organoleptic properties of materials can be represented by the formula

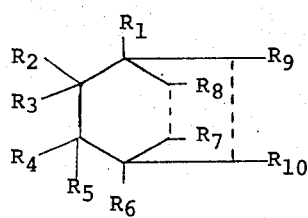

wherein the dashed lines represent single or double carbon-to-carbon bonds; one of $R_2$ and $R_3$ is hydrogen or alkyl and the other is hydrogen or hydroxy or, taken together, $R_2$ and $R_3$ are a carbonyl oxygen; $R_4$ and $R_5$ are alkyl; $R_1$, $R_6$, $R_7$, and $R_8$ are hydrogen or alkyl; and one of $R_9$ and $R_{10}$ is hydrogen, alkyl cyano, carboalkoxy, or aliphatic acyl and the other is hydrogen, at least five of $R_1$ through $R_{10}$, inclusive, being other than hydrogen.

It will be understood from the present description that when one double bond is present, it will link the carbon atoms upon which $R_7$ and $R_8$ are substituent, thus:

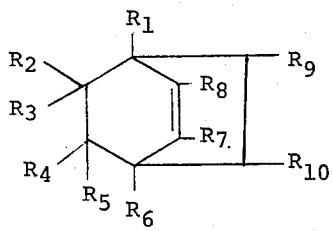

The basic structure when there are two double bonds present is

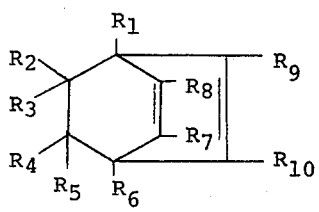

In the present disclosure, $R_1$ through $R_{10}$, inclusive, have the meaning as aforesaid.

Desirable compounds prepared according to the present invention include:

1,3,3,4,5,6-Hexamethylbicyclo-[2.2.2]-oct-5-en-2-one with the formula

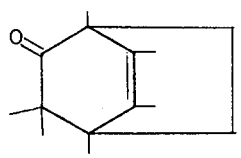

(I)

1,2,3,3,4,5,6-Heptamethylbicyclo-[2.2.2]-oct-5-en-2-ol having the formula

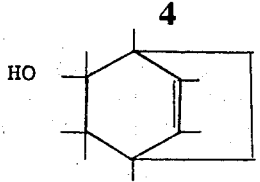

(II)

Carbomethoxylated 1,3,3,5-tetramethylbicyclo-[2.2.2]-octenes, and more specifically the 7-carbomethoxy derivative having the formula

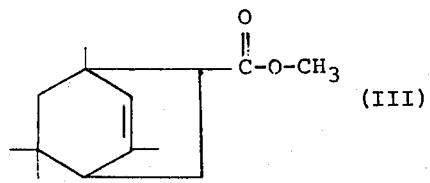

(III)

and the 8-carbomethoxy derivative having the formula

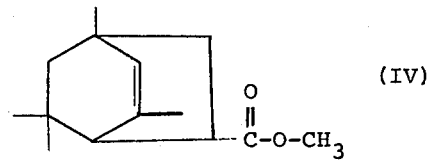

(IV)

Carbomethoxy 1,3,3,5-tetramethylbicyclo-[2.2.2]-octanes, and more specifically the 7-carbomethoxy derivative having the formula

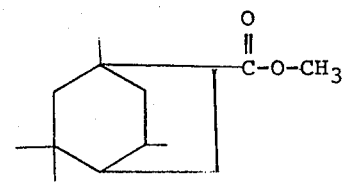

(V)

and the 8-carbomethoxy derivative having the formula

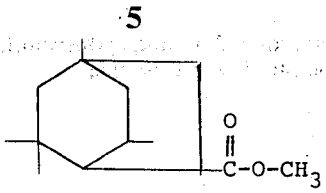 (VI)

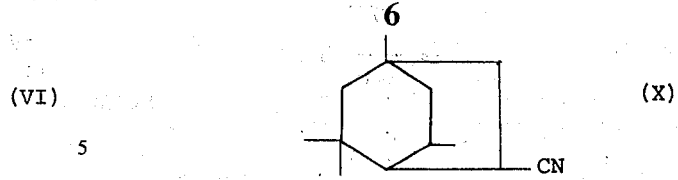 (X)

The cyano derivatives of 1,3,3,5-tetramethylbicyclo-[2.2.2]-octenes, and more specifically the 7-cyano derivative having the formula The acetyl derivatives of 1,3,3,5-tetramethylbicyclo-[2.2.2]-octenes, and more specifically the 7-acetyl derivative having the formula

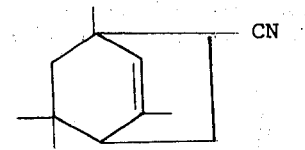 (VII)

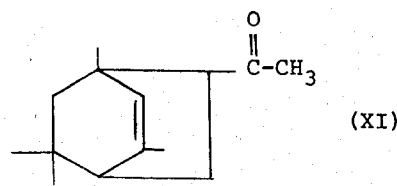 (XI)

and the 8-cyano derivative having the formula and the 8-acetyl derivative having the formula

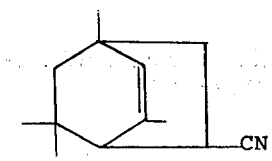 (VIII)

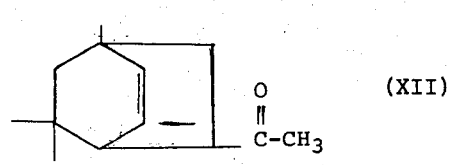 (XII)

The cyano derivatives of 1,3,3,5-tetramethylbicyclo-[2.2.2]-octanes, and more specifically the 7-cyano derivative having the formula The isopropyl derivatives of 1,3,3-trimethylbicyclo-[2.2.2]-octa-5,7-dien-2-one, and more specifically 5-isopropyl-1,3,3-trimethylbicyclo-[2.2.2]-octa-5,7-dien-2-one having the formula

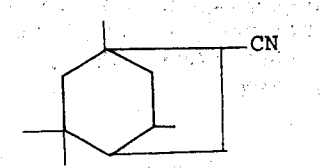 (IX)

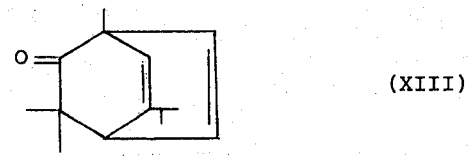 (XIII)

and the 8-cyano derivative having the formula and 6-isopropyl-1,3,3-trimethylbicyclo-[2.2.2]-octa-5,7-dien-2-one having the formula

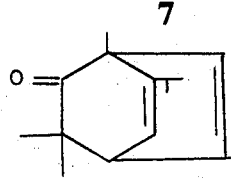

(XIV)

and 6-isopropyl-3,3-dimethylbicyclo-[2.2.2]-octa-5,7-dien-2-one having the formula

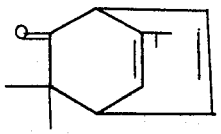

(XVIII)

The isopropyl derivatives of 1,3,3-trimethylbicyclo-[2.2.2]-octan-2-one and more specifically 5-isopropyl-1,3,3-trimethylbicyclo-[2.2.2]-octan-2-one having the formula The isopropyl derivatives of 3,3-dimethylbicyclo-[2.2.2]-octan-2-one and more specifically 5-isopropyl-3,3-dimethylbicyclo-[2.2.2]-octan-2-one having the formula

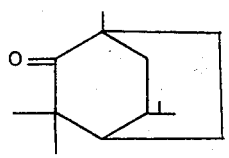

(XV)

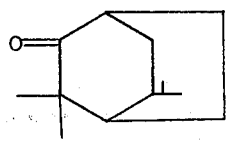

(XIX)

and 6-isopropyl-1,3,3-trimethylbicyclo-[2.2.2]-octan-2-one having the formula and 6-isopropyl-3,3-dimethylbicyclo-[2.2.2]-octan-2-one having the formula

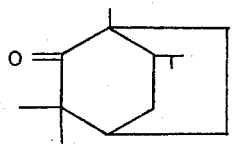

(XVI)

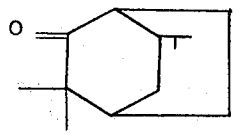

(XX)

The isopropyl derivatives of 3,3-dimethylbicyclo-[2.2.2]-octa-5,7-dien-2-one, and more specifically 5-isopropyl-3,3-dimethylbicyclo-[2.2.2]-octa-5,7-dien-2-one having the formula The isopropyl derivatives of 1,2,3,3-tetramethylbicyclo-[2.2.2]-octan-2-ol and more specifically 5-isopropyl-1,2,3,3-tetramethylbicyclo-[2.2.2]-octan-2-ol having the formula

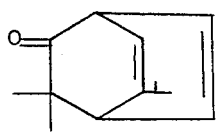

(XVII)

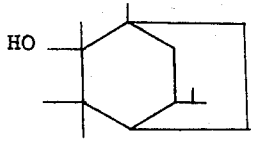

(XXI)

and 6-isopropyl-1,2,3,3-tetramethylbicyclo-[2.2.2]-octan-2-ol having the formula

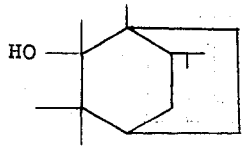 (XXII)

The isopropyl derivatives of 2,3,3-trimethylbicyclo-[2.2.2]-octan-2-ol and more specifically 5-isopropyl-2,3,3-trimethylbicyclo-[2.2.2]-octan-2-ol having the formula

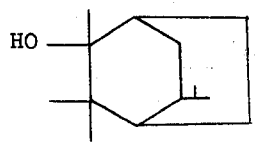 (XXIII)

and 6-isopropyl-2,3,3-trimethylbicyclo-[2.2.2]-octan-2-ol having the formula

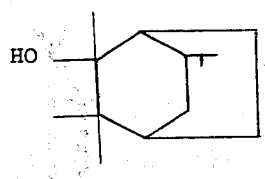 (XXIV)

The isopropyl derivatives of 3,3-dimethylbicyclo-[2.2.2]-oct-5-en-2-one and more specifically 5-isopropyl-3,3-dimethylbicyclo-[2.2.2]-oct-5-en-2-one having the formula

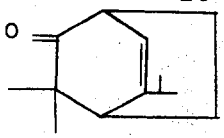 (XXV)

and 6-isopropyl-3,3-dimethylbicyclo-[2.2.2]-oct-5-en-2-one having the formula

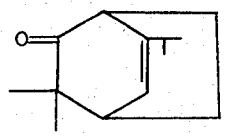 (XXVI)

1,3,3,4,5,6-Hexamethyl-2-ethylbicyclo-[2.2.2]-oct-5-en-2-ol having the formula

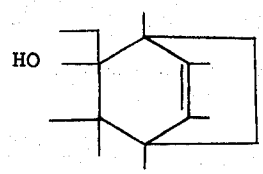 (XXVII)

1,3,3,4,5,6-Hexamethylbicyclo-[2.2.2]-oct-5-en-2-ol having the formula

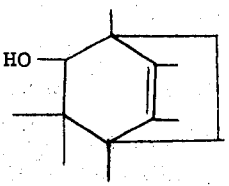 (XXVIII)

The methyl derivatives of 1,3,3,4,5,6-hexamethylbicyclo-[2.2.2]-oct-5-en-2-one and more specifically 1,3,3,4,5,6,7-heptamethylbicyclo-[2.2.2]-oct-5-en-2-one having the formula

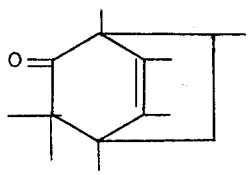

(XXIX)

and 1,3,3,4,5,6,8-heptamethylbicyclo-[2.2.2]-oct-5-en-2-one having the formula

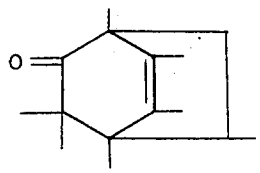

(XXX)

The methyl derivatives of 1,2,3,3,4,5,6-heptamethyl-bicyclo-[2.2.2]-oct-5-en-2-ol and more specifically 1,2,3, 3,4,5,6,7-octamethylbicyclo-[2.2.2]-oct-5-en-2-ol having the formula

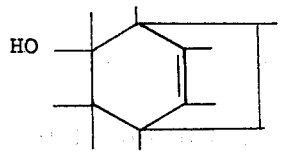

(XXXI)

and 1,2,3,3,4,5,6,8-octamethylbicyclo-[2.2.2]-oct-5-en-2-ol having the formula

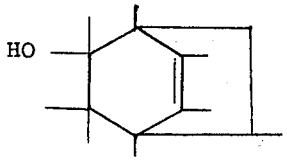

(XXXII)

2-n-Butyl-1,3,3-trimethylbicyclo-[2.2.2]-oct-5-en-2-ol having the formula

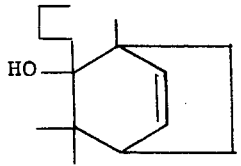

(XXXIII)

It will be apparent to those skilled in the art from the present disclosure that the foregoing compounds can exist as various diastereoisomers and the foregoing formulas are intended to encompass the isomeric forms of the compounds. By way of illustration, a particularly preferred compound, (II), can exist in the forms

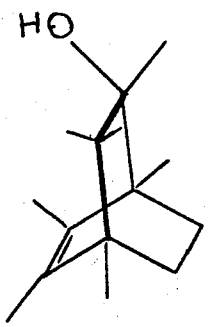

(II(a))

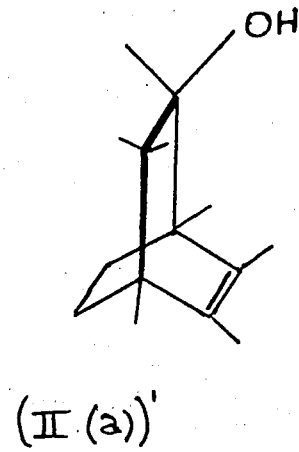

(II(a))'

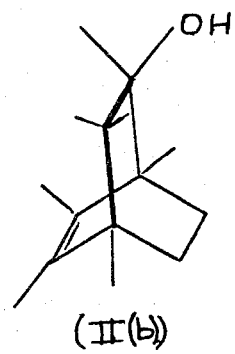

(II(b))

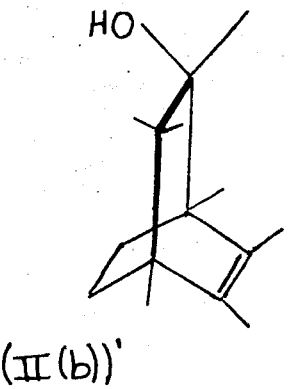

(II(b))'

The foregoing representation sets forth the differences in various diastereoisomers of (II) by way of three dimensional representations.

As taught hereinafter, the compounds of the present invention have certain woody, precious wood and camphoraceous type odors and flavors which suit them for altering organoleptic properties of consumable materials. Particularly desirable materials are those in which the alkyl groups and alkoxy groups are lower alkyl, preferably those having one to four carbon atoms. In certain particularly preferred embodiments, $R_4$ and $R_5$ are methyl.

It will be appreciated from the present disclosure that the bicyclo-[2.2.2]-octane derivatives and mixtures thereof according to the present invention can be used to alter, vary, fortify, modify, enhance, or otherwise improve the organoleptic properties, including aroma and/or flavor, of a wide variety of materials which are ingested, consumed, or otherwise organoleptically sensed. The term "alter" in its various forms will be understood herein to mean the supplying or imparting an aroma or flavor character or note to an otherwise bland, relatively odorless or tasteless substance, or augmenting an existing characteristic where the natural aroma or flavor is deficient in some regard, or supplementing the existing aroma or flavor impression to modify the organoleptic character. The materials which are so altered are generally referred to herein as consumable materials.

The bicyclo-[2.2.2]-octane derivatives of this invention are accordingly useful individually or in admixture as fragrances. They can be used to contribute various woody, camphoraceous, patchouli or floral fragrances. As olfactory agents, the derivatives of this invention can be formulated into or used as components of a "perfume composition".

A perfume composition is composed of a small but effective amount of a bicyclo-[2.2.2]-octane derivative according to this invention and an auxiliary perfume ingredient, including, for example, alcohols, aldehydes, ketones, nitriles, esters, and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation, and (d) top-notes which are usually low-boiling fresh smelling materials.

In perfume compositions the individual component will contribute its particular olfactory characteristics, but the overall effect of the perfume composition will be the sum of the effect of each ingredient. Thus, the individual derivatives of this invention, or mixtures thereof, can be used to alter the aroma characteristics of a perfume composition, for example, by high-lighting or moderating the olfactory reaction contributed by another ingredient in the composition.

The amount of the compounds of this invention which will be effective in perfume compositions depends on many factors, including the other ingredients, their amounts and the effects which are desired. It has been found that perfume compositions containing as little as 0.1 percent of the compounds of this invention, or even less, can be used to impart a scent odor to soaps, cosmetics, and the other products. The amount employed can range up to five percent or higher of the fragrance components and will depend on considerations of cost, nature of the end product, the effect desired on the finished product and the particular fragrance sought.

The derivatives of this invention can be used alone or in a perfume composition as an olfactory component in detergents and soaps; space odorants and deodorants; perfumes; colognes; toilet waters; bath preparations such as bath oil and bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 50 ppm of one or more of the preferred hexamethyl-bicyclo-[2.2.2]-octenol derivative will suffice to impart a floral, woody odor character. Generally, no more than five percent is required in the perfume composition. All parts, percentages, proportions, and ratios herein are by weight unless otherwise indicated.

In addition, the perfume composition or fragrance composition can contain a vehicle or carrier for the bicyclo-[2.2.2]-octane derivatives alone or with other ingredients. The vehicle can be a liquid such as alcohol, glycol, or the like. The carrier can be an absorbent solid such as gum or components for encapsulating the composition.

Such bicyclo-[2.2.2]-octane derivatives are also useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and diary products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products include those designed or used for smoking such as in cigarette, cigar, and pipe tobacco, as well as products such as snuff, chewing tobacco, and the like.

When the bicyclo-[2.2.2]-octane derivatives according to this invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

Such conventional flavoring material include saturated, unsaturated, fatty and amino acids; alcohols, including primary and secondary alcohols; esters, carbonyl compounds, including ketones and aldehydes; lactones; cyclic organic materials including benzene derivatives, alicyclics, heterocyclics such as furans, thiazoles, thiazolidines, pyridines, pyrazines and the like; other sulfur-containing materials including thiols, sulfides, disulfides and the like; proteins; lipids; carbohydrates; so-called flavor potentiators such as monosodium glutamate, guanylates, and inosinates; natural flavoring materials such as cocoa, vanilla, and caramel; essential oils and extracts such as anise oil, clove oil, and the like; artificial flavoring materials such as vanillin; and the like.

It has been found in certain preferred embodiments that various adjuvants are particularly suited for use with derivatives according to the present invention. In view of the utility of compounds according to the present invention for woody, beverage flavors and for enhancing such flavors, it is preferred in certain embodiments that the bicyclo-[2.2.2]-octane derivative or derivatives be combined with one or more adjuvants such as ethyl-2-methylbutyrate, butyl valerate, 2,3-diethyl pyrazine, benzaldehyde, cyclotene(2-hydroxy-3-methyl-2-cyclopenten-1-one) and/or vanillin.

Stabilizers include preservatives such as sodium chloride, and the like, antioxidants such as calcium and sodium ascorbate, ascorbic acid, butylated hydroxyanisole, butylated hydroxytoluene, propyl gallate and the like, sequestrants such as citric acid, EDTA, phosphates, and the like.

Thickeners include carriers, binders, protective colloids, suspending agents, emulsifiers, and the like, such as agar-agar, carrageenan, cellulose and cellulose derivatives such as carboxymethyl cellulose and methyl cellulose, and the like, and other proteinaceous materials, lipids, carbohydrates, starches and pectins.

Surface active agents include emulsifying agents such as mono- and/or diglycerides of fatty acids including capric acid, caprylic acid, palmitic acid, myristic acid, oleic acid, and the like, lecithin, defoaming and flavor-dispersing agents such as sorbitan monostearate, potassium stearate, hydrogenated tallow alcohol, and the like.

Conditioners include compounds such as bleaching and maturing agents such as benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents such as sodium acetate, ammonium bicarbonate, ammonium phosphate, citric acid, lactic acid, vinegar and the like; colorants such as carminic acid, cochineal, turmeric, curcumin, approved food and drug dyes, and the like; firming agents such as aluminum sodium sulfate, calcium chloride and calcium gluconate; texturizers; anti-caking agents such as aluminum calcium sulfate and tribasic calcium phosphate; enzymes; yeast foods such as calcium lactate and calcium sulfate; nutrient supplements such as iron salts including ferric phosphate, ferric pyrophosphate, ferrous gluconate and the like, riboflavin, vitamins, zinc sources such as zinc chloride, zinc sulfate, and the like.

The bicyclo-[2.2.2]-octane derivatives, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The compounds according to this invention can be incorporated with the carriers by conventional means such as spray-drying, drum-drying, and the like. Such carriers can also include materials for coacervating the bicyclo-[2.2.2]-octane derivatives (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

It will be understood by those skilled in the art that the bicyclo-[2.2.2]-octane derivatives according to the present invention can be added to the materials to be flavored at any convenient point in the production of the finished product. Thus, when the derivatives are used to alter or otherwise vary the flavor of the foodstuff, they can be added in the original mixture, dough, emulsion, batter, syrup, or the like prior to any cooking or heating operation. Alternatively, they can be added at a later stage of processing if volatilization losses would be excessive during the earlier processing.

When the derivatives are used to treat tobacco products for example, the additive can be applied in a suitable manner, as by spraying, dipping, or otherwise. They can be applied during the "casing" or final spray treatment of the tobacco, or they can be applied at some earlier stage of curing or preparation. The quantity of bicyclo-[2.2.2]-octane derivatives or mixtures thereof utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff, tobacco product, or other consumable product; the amount and type of flavor initially present in the product; the further process or treatment steps to which the product will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount " is understood in the context of the present invention to be quantitatively adequate to alter the flavor of the foodstuff, tobacco, or other consumable material.

It is accordingly preferred that the ultimate compositions contain from about 0.1 parts per million (ppm) to about 250 ppm of bicyclo-[2.2.2]-octane derivative or derivatives. More particularly, in food compositions it is desirable to use from about 0.5 ppm for enhancing flavors and in certain preferred embodiments of the invention, from about 1 to 25 ppm of the derivatives are included to add positive flavors to the finished product. On the other hand, tobacco compositions can contain as little as 0.5 ppm and as much as 200 ppm depending upon whether a cigarette tobacco, a pipe tobacco, a cigar tobacco, a chewing tobacco, or snuff is being prepared.

The amount of bicyclo-[2.2.2]-octane derivative or derivatives to be utilized in flavoring compositions can be varied over a wide range depending upon the particular quality to be added to the foodstuff, tobacco, or other consumable material. Thus, amounts of one or more derivatives according to the present invention from about 1 ppm up to 80 to 90 percent can be incorporated in such compositions. It is generally found to be desirable to include from about 5 ppm to about 0.1 percent of the derivatives in such compositions.

It will thus be apparent that the derivatives according to the present invention can be utilized to alter the sensory properties, particularly organoleptic properties such as flavor and/or fragrance of a wide variety of consumable materials.

The bicyclo-[2.2.2]-octane ring structure is formed by the reaction of a dienophile with an alkyl-substituted cyclohexa-2,4-dienone having the formula

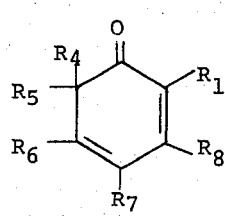

where $R_1$ and $R_4$ through $R_8$ have the meaning given above. Such cyclohexadienone compounds are known and others which are required to carry out processes of this invention can be produced by oxidation of substituted benzene compounds. Such reactions will be apparent to those skilled in the art from a consideration of the present disclosure.

The dienophiles for reaction with the cyclohexadienone are desirably unsaturated compounds having the formula $R_9$-CH=CH-$R_{10}$ or the formula $R_9$-C≡C-$R_{10}$, $R_9$ and $R_{10}$ are as stated herein.

With the former dienophile a bicyclo-[2.2.2]-octa-5-ene will be obtained, while with the latter dienophile a bicyclo-[2.2.2]-octa-5,7-diene will be obtained. The substituents represented by $R_9$ and $R_{10}$ are chosen to provide the desired final bicyclo-octane derivative.

When the bicyclic compound is to be substituted with alkyl materials then alkylene substances are used. In certain preferred embodiments of the invention the dienophile is ethylene, propylene, butylene, or isobutylene. When a carboalkoxy compound is to be prepared, an alkyl acrylate ester is utilized and when a cyano group is desired acrylonitrile or a derivative thereof is used.

When it is desired to obtain a bicyclo-[2.2.2]-octadiene, acetylene or a derivative thereof can be used. Thus, in a preferred embodiment an alkyl-substituted alkyne derivative, particularly 3-methyl-1-butyne can be utilized.

The Diels-Alder conditions for the formation of the bicyclo-[2.2.2]-octane derivative can be varied depending upon the particular cyclohexadienone and dienophile utilized and upon the other factors herein described. Stoichiometric quantities of reactants are used, although in certain embodiments it is desirable to use a moderate excess, up to 25 percent, of the dienophile.

The tricyclic ring formation can be carried out with just the two reactants, but it is frequently desirable to utilize a reaction vehicle. Such a vehicle can function as a solvent for the reactants, to moderate the course of the reaction, to provide more intimate contact between the reactants, and to improve control over parameters such as temperature and pressure. The reaction vehicle should be inert and is desirably one in which both reactants are soluble. In certain embodiments of the invention it is desirable to use an aromatic hydrocarbon such as benzene or a substituted aromatic, particularly an alkyl-substituted benzene such as toluene, xylene, or the like.

The pressure under which the Diels-Alder reaction is carried out can vary over a range and is desirably superatmospheric. Pressures of from 150 to 400 psig are desirably used in certain embodiments.

The Diels-Alder reaction can be carried out at temperatures of from about 150°C to about 300°C. Below the aforesaid lower temperature the reaction proceeds at a very low rate. On the other hand, at temperatures considerably higher than those preferred, the reaction may proceed uncontrollably and/or produce a relatively large quantity of unwanted by-products which lower the yield of desirable materials and complicate purification of the product. The temperature chosen will thus depend upon the particular reactants utilized. The preferred temperatures for use with dienophiles which are liquid at normal temperatures are from about 190°C to 250°C. The product of the dienophile-cyclohexadiene reaction can be purified and/or isolated by conventional methods as hereinafter mentioned.

To obtain the novel alcohols according to the present invention the polyalkylbicyclo-[2.2.2]-octadienone or -octenone is reacted with an organometallic compound. When it is desired to obtain an alcohol wherein $R_2$ or $R_3$ is hydrogen and the other is hydroxyl, an alkali metal hydride is used. A preferred hydride for use in carrying out the present invention is an alkali metal aluminum hydride, a preferred hydride being lithium aluminum hydride.

When it is desired that one of $R_2$ and $R_3$ is alkyl and the other is hydroxyl, then a metallo alkyl compound can be used. The metallo alkyl compound for use herein can be an alkyl Grignard reagent such as alkyl magnesium halide, where the halide is the chloride, bromide or iodide. The lower alkyl magnesium chlorides are preferred and methyl magnesium chloride, ethyl magnesium chloride, propyl magnesium chloride, and butyl magnesium chloride are especially preferred in certain embodiments.

The organometallic compounds also include lower alkyl alkali metal compounds when it is desired that one of $R_2$ and $R_3$ be alkyl. Preferred compounds include ethyl and methyl lithium.

The reaction with the metallic compounds is desirably carried out in a vehicle. Preferred vehicles are polar organic solvents, although aromatic solvents can also be used. The preferred reaction vehicles are cyclic ethers such as tetrahydrofuran; cyclic polyethers such as dioxane; linear ethers such as diethyl ether, and linear polyethers such as Diglyme diethylene glycol dimethyl ether. The reaction vehicle can also comprise phosphorus materials such as hexamethyl phosphoramide and the like.

The reaction vehicle, as noted above, can also include aromatic solvents, particularly monocyclic materials such as benzene, toluene, and the like.

The reaction with the organometallic compound is desirably carried out at temperatures of from 10°C to about 125°C. The use of temperatures substantially below this desirable range results in extremely low reaction rates and the use of temperatures substantially above this range can result in undesirable by-products and unnecessarily high pressures. It is accordingly preferred to use temperatures in the range of from 40°C to 100°C, and in many of the preferred embodiments temperatures of from 60°C to 100°C are utilized.

The reaction can be carried out under a wide range of presssures, depending on temperature, reactants, and vehicles, but atmospheric and super-atmospheric pressures are preferred.

The quantity of organometallic material reacting with the bicyclo-octanone derivative can be varied over a wide range. It is desirable to use at least a stoichiometric quantity of organometallic compound, and quantities up to 250 percent of such theoretical amount can be utilized, that is, a 150 percent excess. In general, it is desirable to use from about 125 percent to about 200 percent of the theoretical amount of organometallic compound to insure good reaction rate and completeness.

The time required for the reaction will vary depending upon the temperature, reactants, pressure and the like. Ordinarily, reaction times of from abut two to about 24 hours are desirable. It will be understood from the present disclosure that temperatures of 100°C will permit obtaining good yields of salt corresponding to the alcohol in four hours with relatively small excesses of organometallic compounds, whereas longer times of 16 to 20 hours can be required with temperatures of 60°C.

After the reaction with the organometallic compound is completed to the extent desired, the product is then hydrolyzed by acidification or basification to obtain the alcohol itself. A base or an acid can be added to water and then this can be used to wash ahd hydrolyze the salt, the product of the reaction. Such hydrolysis can be carried out over a wide range of temperatures from 5°C to about 100°C, and temperatures of 15°C to about 30°C are preferred. In certain embodiments of the invention the hydrolysis is carried out with an acidic medium, such as a saturated ammonium chloride solution.

The saturated ring derivatives are produced by hydrogenation of the bicyclo-[2.2.2]-octadiene or bicyclo-[2.2.2]-octene derivatives with gaseous hydrogen. The hydrogenation is desirably carried out at superatmospheric pressures of 150 to 600 psig, and preferably from 200 to 400 psig to provide a good reaction rate without substantial production of unwanted byproducts.

The temperature is chosen so as to provide reaction times of about one to eight hours and preferably two to six hours. Accordingly, the temperatures utilized are in the range of 80°C to 210°C, and preferably from 100°C to 160°C.

The hydrogenation is desirably carried out in the presence of an inert vehicle, desirably a lower aliphatic alcohol. Preferred vehicles are ethanol, propanol, and isopropanol. The reaction is carried out in the presence of a catalyst, and the metallic hydrogenation catalysts such as nickel or precious metals such as platinum and palladium. The metallic catalyst can be utilized on a carrier, and a 5 percent palladium on carbon catalyst is utilized in certain preferred embodiments of the present invention.

The intermediate and/or final products obtained can be purified or isolated by conventional purification after appropriate washing, neutralizing and/or drying as appropriate. Thus, such products can be purified and/or isolated by distillation, steam distillation, vacuum distillation, extraction, preparative chromatographic techniques, and the like.

The following examples are given to illustrate embodiments of the invention as it is presently preferred to practice it. It will be understood that these examples are illustrative, and the invention is not to be considered as restricted thereto except as indicated in the appended claims.

EXAMPLE I

Preparation of
2,3,4,5,6,6-Hexamethylcyclohexa-2,4-dien-1-one

A three-liter reaction flask is charged with 360 ml of acetic anhydride cooled to −5°C, and 90 ml of concentrated sulfuric acid is added slowly while maintaining the temperature of the solution below 0°C. Thereafter, 84 ml of 30 percent hydrogen peroxide is added at −5°C during 25 minutes. The resulting white slurry is dissolved in 250 ml of methylene chloride.

The methylene chloride solution is added dropwise in three minutes at 0°C to a solution of 80 g of hexamethylbenzene, 300 ml of methylene chloride, 360 ml of acetic acid, and 270 ml of concentrated sulfuric acid. The mixture is stirred at 0°–5°C for 90 minutes and the resulting yellow solution is poured into 1500 ml of ice-water.

The aqueous layer is separated and extracted three times with 500 ml portions of methylene chloride. The combined methylene chloride layer and extracts are washed twice with one-liter portions of water, once with one-liter of 5 percent aqueous sodium hydroxide solution, once with one-liter of saturated ferrous ammonium sulfate solution, and twice more with water. The methylene chloride solution is dried over magnesium sulfate and distilled from the filtered solution to give 85 g of a slightly yellow oil.

Fractional distillation over a twelve-inch Vigreaux column gives 76.0 g of 2,3,4,5,6,6-hexamethylcyclohexa-2,4-dien-1-one boiling at 75°–90°C at 0.5 mm Hg.

The infrared spectrum of 2,3,4,5,6,6-hexamethylcyclohexa-2,4-dien-1-one shows absorptions at 2880-2980, 1620-1660, 1560-1540 (shoulder), 1450, 1370, 1335, 1285, 1262, 1215, 1100, 1070, 1060, 985, 945, 900, 790, 630, and 600 $cm^{-1}$.

The nuclear magnetic resonance (NMR) spectrum ($CDCl_3$) shows a 6H singlet at 1.14$\delta$, and a 3H singlet at 2.02$\delta$. The mass spectrum exhibits a molecular ion at m/e (ratio of mass to charge) of 178.

EXAMPLE II

Preparation of 1,3,3,4,5,6-Hexamethylbicyclo-[2.2.2]-oct-5-en-2-one

A solution of 70 g of 2,3,4,5,6,6-hexamethylcyclohexa-2,4-dien-1-one in 300 ml of benzene is placed in a two-liter Parr stirred autoclave and the air is removed by passing ethylene through the reaction vessel. Ethylene is charged to obtain a 180 psig (pounds per square inch, gauge) pressure at room temperature and then heated to 200°C for 2-½ hours. The internal pressure increases to a maximum of 400 psi and drops to 340 psi. After cooling to room temperature the benzene is distilled under reduced pressure to give 85 g of a light yellow oil comprising Compound (I).

This material has a woody, pine cone, warm aroma.

The infrared spectrum of the 1,3,3,4,5,6-hexamethylbicyclo-[2.2.2]-oct-5-en-2-one exhibits absorptions at 2860-2970, 1710, 1470, 1455, 1440, 1380, 1375, 1370, 1355, 1260, 1230, 1205, 1140, 1100, 1062, 1055, 1030, and 1010 $cm^{-1}$. The NMR spectrum shows singlet methyl signals at 0.88, 0.93, 1.07, and 1.12$\delta$. The C-5 and C-6 methyls appear at 1.70 and 1.62$\delta$ respectively. The mass spectrum shows a molecular ion at m/e 206.

EXAMPLE III

Preparation of 1,2,3,3,4,5,6-Heptamethylbicyclo-[2.2.2]-oct-5-en-2-ol

A three molar solution (170 ml) of methyl magnesium chloride in tetrahydrofuran is heated to reflux under nitrogen and a solution of 85 g of 1,3,3,4,5,6-hexamethylbicyclo-[2.2.2]-oct-5-en-2-one in 250 ml of tetrahydrofuran is added dropwise over a twenty-minute period and the reaction mixture is refluxed under nitrogen for an additional two hours. An extra 50 ml of methyl magnesium chloride in 50 ml of tetrahydrofuran is added and the reaction mixture refluxed for 12 hours.

The excess Grignard reagent and salts are then hydrolyzed with saturated ammonium chloride solution, added slowly with ice bath cooling, and the tetrahydrofuran solution is decanted from the salts. The tetrahydrofuran is distilled from the product under reduced pressure to yield 75 g of yellow oil. The crude alcohol is distilled over a 12-inch Goodloe packed column at a 4:1 reflux ratio, and a product boiling at 80°–87°C at 0.5 mm Hg is collected. Recrystallization of the solid fractions from hexane provides a white crystalline solid melting at 72°–73°C.

The solid has an excellent woody, camphoraceous odor and is quite similar to patchouli alcohol.

Gas-liquid chromatographic (GLC) analysis of the recrystallized product shows the presence of two epimeric alcohols, A (Compounds IIa and IIa') and B (Compounds IIb and IIb'), in the ratio of 1:12.5.

The infrared spectrum of the major alcohol A exhibits absorptions at 3630, 3520, 2860-3000, 1470, 1440, 1390, 1383, 1379, 1368, 1300, 1190, 1180, 1150, 1118, 1099, 1078, 1059, 1050, 1000, 986, 907, and 798 $cm^{-1}$. In the NMR spectrum of the major component (A) five methyl (3H) singlets appear at 0.95$\delta$, 1.27$\delta$, 1.38$\delta$, 1.46$\delta$, and 1.68$\delta$. A methyl singlet (6H) appears at 2.82$\delta$. The mass spectrum of A shows a molecular ion at m/e 222.

The infrared spectrum of the minor alcohol component (B) exhibits absorptions at 3580, 3510, 2860-3000, 1470, 1440, 1390, 1378, 1362, 1316, 1297, 1242, 1210, 1184, 1145, 1119, 1098, 1075, 1060, 1050, 1040, 1030, 1000, 910, 880, 800, 740, 708, 680, 615, and 580 $cm^{-1}$. The NMR spectrum of the minor component (B) shows methyl singlets (3H) at 0.86$\delta$, 1.23$\delta$, 1.46$\delta$, 1.55$\delta$, 1.60$\delta$, 2.88$\delta$, and 2.93$\delta$. The mass spectrum shows a molecular ion at m/e 222.

EXAMPLE IV

Preparation of 1,3,3,5-Tetramethyl-7- and 8-carbomethoxybicyclo-[2.2.2]-oct-5-ene A two-liter autoclave is charged with 68 g of 1,3,5,5-tetramethylcyclohexa-1,3-diene, 45 g of methyl acrylate, and 100 ml of benzene, and the mixture is heated at 200°C for 9 hours. The solvent is removed by flash-evaporation under reduced pressure to net 102 g of crude product. Fractional distillation over a three-inch micro-Vigreaux column yields 34 g of an oil boiling at 76°–145°C at 1.2 mm Hg. Gas-liquid chromatography shows the presence of four components: major component B (Compound III) and three minor components A, C, and D (Compound IV). The mixture has a green, minty, valerian aroma.

The infrared spectrum of the major component B exhibits absorptions at: 3025, 2920, 2870, 1870, 1700, 1460, 1450, 1440, 1430, 1375, 1360, 1340, 1320, 1285, 1270, 1250, 1215, 1197, 1160, 1130, 1105, 1020, 990, 980, 920, 800, and 740 $cm^{-1}$.

The NMR spectrum of the major component B shows 3H singlets at 0.78, 0.98, 1.02, 2.00, and 3.56$\delta$; and a 1H singlet at 5.38$\delta$.

The infrared spectrum of component C exhibits absorptions at: 2950, 2860, 1735, 1440, 1360, 1250, 1200, 1170, 1155, 1060, 1020, 1000, 880, and 830 $cm^{-1}$.

The nuclear magnetic resonance spectrum of component C shows 3H singlets at 0.92, 1.74, and 3.64$\delta$; and 1H singlets at 5.02 and 5.48$\delta$.

The infrared spectrum of component D exhibits absorptions at 3070, 2950, 1735, 1650, 1605, 1430, 1360, 1310, 1275, 1240, 1215, 1190, 1140, 1130, 1060, 1040, 1010, 990, 940, 880, 850, 810, 640, and 570 $cm^{-1}$.

The nuclear magnetic resonance spectrum of component D shows 3H singlets at 0.82, 0.92, 0.98, 1.69, and 3.62δ; a 2H doublet at 4.67δ; and a 1H singlet at 5.76δ.

The mass spectrum of the major component B exhibits a molecular ion at m/e 222, as does component D.

The mass spectrum of the component(s) C shows species with as high an m/e as 236 and 238. Thus, component C is probably a mixture of components of uncertain molecular weights.

EXAMPLE V

Preparation of 1,3,3,5-Tetramethyl-7-carbomethoxy-bicyclo-[2.2.2]-octane and 1,3,3,5-Tetramethyl-8-carbomethoxybicyclo-[2.2.2]-octane A two-liter autoclave is charged with 3.0 g of a mixture of 1,3,3,5-tetramethyl-7 and 8-carbomethoxybicyclo-[2.2.2]-oct-5-ene, 200 ml of isopropyl alcohol, and 0.05 g of 5 percent palladium on carbon catalyst and purged with hydrogen gas and then pressurized to 200 psig. The reaction vessel is heated to 100°C (200 psig) for six and one-half hours and then allowed to stand until cooled to room temperature.

The catalyst is filtered from the solution, and the solvent removed by flash evaporation under reduced pressure to net 3.0 g of crude product. GLC shows two significant peaks which are trapped for spectral data and odor evaluation. The spectral data indicate that these two components are most likely conformational isomers. The fragrances of these components are fruity, green, minty, fig-like, and woody.

The infrared spectrum of the major component A (Compound V) exhibits absorptions at: 2980-2860, 1725, 1460, 1430, 1360, 1340, 1320, 1280, 1260, 1240, 1210, 1190, 1160, 1130, 1115, 1085, 1060, 1035, 1020, 995, 978, 930, 912, 890 820, 812, 780, and 740 cm$^{-1}$.

The NMR spectrum of the major component A shows 3H singlets at 0.70, 1.05, and 3.59δ; a 6H singlet at 0.96δ and a 3H doublet at 1.01δ. The mass spectrum exhibits a molecular ion at m/e 224.

The infrared spectrum of the minor component(s) B exhibits absorptions at: 2960-2860, 1730, 1455, 1430, 1380, 1360, 1318, 1262, 1255, 1235, 1210, 1200, 1190, 1160, 1070, 1050, 1020, 1005, 915, 900, 830, 800, 780, and 740 cm$^{-1}$. The NMR spectrum indicates that this trapped sample is actually a mixture of two isomers. Methyl signals are found at: 0.73, 0.77, 0.92, 1.03, 1.05, and 1.13δ. A 3H singlet at 3.59δ accounts for the ester methyl. The mass spectrum of this trapping is very close to that for the component A. The molecular ion of Compounds VI and V appears at m/e 224.

EXAMPLE VI

Preparation of 1,3,3,5-Tetramethyl-7 and 8-cyanobicyclo-[2.2.2]-oct-5-ene

A two-liter autoclave is charged with 136 g of 1,3,5,5-tetramethylcyclohexa-1,3-diene, 53 g of acrylonitrile, and 500 ml of benzene and heated to 200°C for 6 hours and then allowed to cool to room temperature. The solvent is flash-evaporated under reduced pressure to net 176.4 g of crude product. Gas-liquid chromatography shows the presence of two major peaks and a small amount of starting material. The crude oil is rushed over a two-inch splash column to yield 139 g boiling 71°–75°C at 0.3 mm Hg. The fragrances of these components are woody, camphoraceous, minty, and floral.

The infrared spectrum of component(s) A (Compound VII) shows absorptions at: 3010, 2960, 2920, 2860, 2230, 1650, 1450, 1380, 1365, 1335, 1315, 1282, 1210, 1190, 1150, 1130, 1040, 1022, 1003, 965, 910, 802, 715, and 660 cm$^{-1}$. The NMR spectrum of component A exhibits 3H singlets at 0.80, 1.12, 1.18, and 1.76δ. The 1H singlet (vinyl proton) is found at 5.42δ. The mass spectrum shows a molecular ion at m/e 189.

The infrared spectrum of components B (Compound VIII) shows absorptions at 3010, 2960, 2910, 2235, 1455, 1450, 1380, 1360, 1340, 1210, 1190, 1160, 1020, 980, 975, 800, and 795 cm$^{-1}$. The NMR spectrum of the component designated as B shows that it is probably a mixture of isomers, since there are an excessive number of methyl group signals. There are four methyl signals that integrate for a total of 9 protons or 3 methyl groups at: 0.79, 0.97, 1.10, and 1.23δ when a fifth methyl signal at 1.81δ is taken as three protons and a vinyl proton signal at 5.48δ is taken as one proton. The mass spectrum is very similar to that of component A in that a molecular ion is again noted at m/e 189.

EXAMPLE VII

Preparation of 1,3,3,5-Tetramethyl-7 and 8-cyanobicyclo-[2.2.2]-octane

A two-liter autoclave is charged with 15.0 g of 1,3,3,5-tetramethyl-7 and 8-cyanobicyclo-[2.2.2]-oct-3-ene, 0.2 g of 5 percent palladium on carbon catalyst and 200 ml of isopropyl alcohol; purged with hydrogen; and then pressurized to 100 psig. The autoclave is heated to 100°C and the contents stirred for 20 hours.

The reaction vessel is allowed to cool to room temperature and the reaction mixture is removed from the vessel and filtered. The solvent is flash-evaporated to give 13 g of crude product. GLC shows two significant peaks, designated as component A and component B. The fragrances are warm, fruity, woody with minty nuances.

The infrared spectrum of component A (Compound IX) exhibits absorptions at: 2960, 2920, 2870, 2230, 1450, 1375, 1370, 1350, 1300, 1275, 1205, 1195, 1170, 1140, 1020, and 960 cm$^{-1}$. The NMR spectrum exhibits 3H singlets at 0.90, 0.95, and 0.98δ. The 3H doublet appears at 1.07δ, and the mass spectrum shows a molecular ion at m/e 191.

The infrared spectrum of component B (Compound X) exhibits absorptions at: 2960, 2920, 2880, 2235, 1460, 1390, 1378, 1360, 1340, 1300, 1260, 1210, 1195, 1175, 1145, 1120, 1000, and 960 cm$^{-1}$. The NMR spectrum exhibits 3H singlets at 0.96, 1.02, 1.07δ and a 3H doublet at 1.10δ. The mass spectrum shows a molecular ion at m/e 191.

EXHIBIT VIII

Preparation of 1,3,3,5-Tetramethyl-7 and 8-acetylbicyclo-[2.2.2]-oct-5-ene

A two-liter autoclave charged with 136 g of 1,3,5,5-tetramethylcyclohexa-1,3-diene, 70 g of methyl vinyl ketone, and 300 ml of benzene is flushed with nitrogen and then heated to 200°C for 5 hours, whereafter the autoclave is allowed to cool to room temperature. The solvent is flash-evaporated under reduced pressure to net 174 g of crude product. The oil is rushed over a two-inch splash column to collect 100 g of material boiling at 68°–125°C at 0.5 mm Hg which is redistilled over a 12-inch Goodloe-packed column to obtain product boiling at 83°–94°C at 0.7 mm Hg. The gas-liquid chromatography shows only two major peaks which are trapped for spectral tests. The material has a fruity, woody aroma with a camphoraceous fragrance note.

The infrared spectrum of component A (Compound XII) shows absorptions at: 3005, 2960, 2920, 2865, 1705, 1445, 1375, 1360, 1270, 1200, 1185, 1165, 1130, 1060, 1030, 980, 940, 900, 840, and 800 cm$^{-1}$. The NMR spectrum shows 3H singlets at 0.73, 1.03, 1.07, 1.72, and 2.06δ; and the 1H singlet appears at 5.43δ. The mass spectrum shows a molecular ion at m/e 206.

The infrared spectrum of component B (Compound XI) shows absorptions at: 2960-2900, 2860, 2810, 1707, 1660, 1600, 1440, 1420, 1360, 1280, 1220, 1180, 1155, 1055, 1040, 1005, 980, 940, 915, 870, 835, 818, 730, 645, 638, 590 and 570 cm$^{-1}$. The NMR shows 3H singlets at 0.75, 1.79, 1.92δ; a 6H singlet at 0.98δ; and a 1H singlet (vinyl) at 5.40δ. The mass spectrum shows a molecular ion at m/e 206.

EXAMPLE IX

Preparation of 5- and 6-Isopropyl-1,3,3-trimethylbicyclo-[2.2.2]-5,7-octadien-2-one A two-liter Parr autoclave is charged with 2.9 g of 2,6,6-trimethyl-2,4-cyclohexadienone dimer, 4.35 g of 3-methyl-1-butyne, and 250 cc of benzene, and the contents are heated at a temperature between 190° and 200°C for 17 hours, while maintaining the pressure in the range of 210–240 psig. The reaction mass is then cooled and the solvent stripped off at 50 mm Hg pressure and 50°C yielding 4.7 g of crude product.

GLC, NMR, and MS (mass spectral) analyses indicate that the product is 5- and 6-isopropyl-1,3,3-trimethylbicyclo-[2.2.2]-5,7-octadien-2-one. The material has a minty, camphoraceous, woody aroma with a spicy (peppery) fragrance note.

MS shows m/e peaks at 70, 119, 41, 42, 91 (molecular weight 204) and NMR shows 1.02 (m,12H), 1.48 (d,3H), 2.42 (m,1H), 3.36 (m,1H), 6.00 (m,2H), 6.50 (m,1H)δ. In this text, "s" is a singlet; "d" a doublet; and "m" a multiplet in NMR spectra.

EXAMPLE X

Preparation of 1,3,3-Trimethyl-5- and 6-isopropylbicyclo-[2.2.2]-octan-2-one

A two-liter Parr autoclave equipped with a hydrogen feed apparatus is charged with 8.6 g of 5- and 6-isopropyl-1,3,3-trimethylbicyclo-[2.2.2]-5,7-octadien-2-one (produced by the procedure of Example IX), 0.5 g of 5 percent palladium on carbon catalyst, and 300 cc of ethanol and maintained for 30 hours at 90°–120°C and 110-240 psig. The catalyst is then filtered off and ethyl alcohol solvent is stripped off at 50 mm Hg pressure and 60°C to yield 25.7 g of material identified by GLC, MS and NMR analyses as 1,3,3-trimethyl-5- and 6-isopropylbicyclo-[2.2.2]-octan-2-one.

The material has a minty, camphoraceous aroma.

The MS analysis shows m/e peaks at 82, 137, 208, 41, 138, 81. The NMR analysis shows 0.7 (m,6H), 0.91 (s,3H), 1.09 (s, 6H), and 1.70 (m,9H)δ.

EXAMPLE XI

Preparation of 3,3-Dimethyl-6-isopropyl-bicyclo-[2.2.2]-octa-5,7-diene-2-one and 3,3-Dimethyl-5-isopropyl-bicyclo-[2.2.2]-octa-5,7-diene-2-one A two-liter Parr autoclave is charged with 25 g (about 0.2 moles) of 6,6-dimethyl-cyclohexa-2,4-dienone, 28 g of 3-methyl-1-butyne, and 300 cc of benzene, and the contents are heated to about 200°C for 11 hours. After heating, the benzene solvent is stripped off under vacuum to yield 34.0 g of product which is distilled under 3 mm Hg pressure to yield a mixture of Compounds (XVII) and (XVIII). The material has a dirty, valerian-like, phenolic, rooty aroma.

The NMR shows 0.9 (5.3H), 0.98 (5.9H), 2.35 (m, 1H), 3.34 (m, 1H), 3.85 (m. 1H), 5.93 (m, 1H), and 6.34 δ (m, 2H).

IR shows a carbonyl absorption at 1710 cm$^{-1}$ and MS analysis shows m/e peaks at 70, 43, 105, 42, and 91.

EXAMPLE XII

Preparation of 5- and 6-Isopropyl-3,3-dimethylbicyclo-[2.2.2]-octan-2-one

A two-liter Parr autoclave is charged with 15 g of 5- and 6-isopropyl-3,3-dimethylbicyclo-[2.2.2]-5,7-octadiene-2-one, 0.5 g of 5 percent palladium on carbon catalyst, and 300 cc of ethanol and hydrogen is charged into the autoclave at 120°–130°C and at 200 psig. The autoclave is heated over a period of 3.5 hours at which point the pressure is allowed to reach 340 psig.

The catalyst is filtered off and the solvent is stripped to yield 15.0 g of product identified by MS and NMR analyses as 5- and 6-isopropyl-3,3-dimethylbicyclo-[2.2.2]-octan-2-one. The material has a dirty, valerian-like aroma.

Mass spectral analysis shows m/e peaks at 123, 41, 69, 65, 82, 194 (molecular). NMR analysis shows 0.79 (d,6H), 1.09 (d,6H), 1.69 (m,9H), and 2.34 (m,1H)δ.

EXAMPLE XIII

Preparation of 5- and 6-Isopropyl-1,2,3,3-tetramethylbicyclo-[2.2.2]-octan-2-ol

A 10 cc micro apparatus is charged with one part by volume of 5- and 6-isopropyl-1,3,3-trimethylbicyclo-[2.2.2]-octan-2-one, four parts by volume of 5 percent methyl lithium in ether, and 6 parts by volume of benzene, and the reactants are heated to reflux and maintained at reflux for two hours whereupon the mixed C-2 epimers of Compounds (XXI) and (XXII) are trapped by GLC.

The mass spectral analysis shows m/e peaks at 86, 71, 43, 41, 95, and 206 (molecular peak).

The material has a buttery, woody aroma.

EXAMPLE XIV

Preparation of 5- and 6-Isopropyl-3,3-dimethylbicyclo-[2.2.2]-octa-5,7-dien-2-one A two-liter Parr autoclave is charged with 25 g (0.2 mole) of 6,6-dimethylhexa-2,4-dienone, 28 g of 3-methyl-1-butyne, and 300 cc of benzene, and heated to 195°C, at which point the pressure is about 200 psig.

After heating at this temperature for several hours the contents are cooled to room temperature and removed from the autoclave.

The benzene solvent is then stripped off under vacuum to yield 34.0 g of crude.

The crude product is then distilled to yield 24.9 g of product, a mixture of Compounds (XXV) and (XXVI), boiling at 92°C and 3 mm Hg. GLC shows two peaks. IR analysis shows a carbonyl peak at 1710 cm$^{-1}$; NMR shows 0.9 (5.3H) 0.98 (5.9H), 2.35 (m, 1H), 3.34 (m,1H), 3.85 (m,1H), 5.93 (m,1H), and 6.34$\delta$ (m,2H). Mass spectral analysis exhibits m/e peaks at 70, 43, 105, 42, and 91.

EXAMPLE XV

Preparation of 5- and 6-Isopropyl-2,3,3-trimethylbicyclo-[2.2.2]-octan-2-ol

A 50 cc micro apparatus is charged with 7 g of 5- and 6-isopropyl-3,3-dimethylbicyclo-[2.2.2]-octan-2-one, 16 g of 5 percent methyl lithium in diethyl ether, and 20 cc of benzene and the contents are refluxed for two hours. An additional 16 g of the methyl lithium ether solution is added and the reactants are refluxed for one hour.

The reaction mass is hydrolyzed with 50 cc of water and washed with one 50 cc portion of saturated sodium chloride solution.

The washed reaction mass is then dried over anhydrous sodium sulfate and stripped of solvent to yield 6.8 g of Compounds (XXIII) and (XXIV) (boiling point 112°C at 2–3 mm Hg).

The material has a camphoraceous odor.

Mass spectral analysis shows m/e peaks at 43, 71, 86, 41, 210 (molecular), and NMR analysis shows 0.90 (m,12H), 1.15 (s,3H), and 1.50$\delta$ (M,10H).

EXAMPLE XVI

Preparation of 1,3,3,4,5,6-Hexamethyl-2-ethylbicyclo-[2.2.2]-oct-5-en-2-ol

A three-neck, round bottom flask is charged with 44 ml of a solution of 1,3,3,4,5,6-hexamethylbicyclo-[2.2.2]-oct-5-en-2-one prepared by the process of Example II in benzene (concentration 1.73 moles in 600 ml of solution), 100 ml benzene is added and the solution is stirred while being cooled to 10°C. Ethyl lithium (100 ml) in benzene (5.1 percent concentration) is added dropwise. An ice bath is used to maintain the temperature at 10°–15°C.

The system is purged with nitrogen to minimize destruction of the ethyl lithium by water vapor. The reaction is slightly exothermic.

GLC analysis indicates three main peaks: unreacted starting material, 45 percent; two isomeric products, 39 percent. To the above mixture another 100 ml of ethyl lithium is added dropwise. The solution is stirred at 10°C for a period of 35 minutes. GLC analysis indicates 90 percent of the subject material and 1.3 percent starting material. After another 30 minutes of stirring, 100 ml of water is added to the reaction mass.

The solution is then poured into a separatory funnel, separated, washed once again with 100 ml of water, and the organic layer is stripped of solvent on a rotary evaporator yielding 22 g of crude product. The crude product in benzene is extracted and washed with sodium hydroxide solution and the organic layer is analyzed via GLC analysis indicating production of the C-2 epimers of Compound (XXVII). The product is then distilled on a micro-Vigreaux column yielding five fractions. The fourth fraction is analyzed by GLC and MS methods.

Mass spectral analysis shows m/e peaks at 136, 119, 41, 219 (molecular), and 203. The epimers have a woody, camphoraceous aroma.

EXAMPLE XVII

Preparation of 1,3,3,4,5,6-Hexamethyl-[2.2.2]-bicyclo-oct-5-en-2-ol

A dry 500 ml three-necked flask is charged with 150 ml of anhydrous diethyl ether and 4.2 g (0.11 mole) of lithium aluminum hydride, and during 1.2 hours at reflux, a mixture of 50 ml anhydrous ethyl ether and 41 g of the product of Example II (1,3,3,4,5,6-hexamethylbicyclo-[2.2.2]-oct-5-en-2-one) is added to the reaction mass. Stirring at reflux is continued for a period of 0.5 hours after completion of the addition and the reaction mixture is sampled on GLC showing 17.9 percent starting material and 40.9 percent and 41.2 percent of two products.

Stirring at reflux is continued for an additional hour, an additional 2.0 g of lithium aluminum hydride is added, and stirring at reflux is continued for 0.5 hours. The mixture is allowed to stand for a period of 14 hours, at the end of which time less than 0.1 percent starting material is determined to exist in the reaction mass.

Approximately 20 ml of water is added dropwise to the reaction mass, the mixture is filtered, and the filtrate is dried over anhydrous magnesium sulfate and then stripped of solvent. The residue, weighing 37.7 g, shows two major peaks on GLC: 48.5 percent and 49.3 percent.

The product is determined by MS and NMR analyses to be 1,3,3,4,5,6-hexamethyl-[2.2.2]-bicyclo-oct-5-en-2-ol. It has a chocolate, basic woody, camphoraceous aroma.

Mass spectral analysis shows m/e peaks at 136, 121, 41, 105, 91, and 208 (molecular). NMR analysis of the (mixture of isomers) shows singlets at 0.94, 1.02, 1.25, 1.42, 1.46, 1.60, 1.80, 2.80, and 2.86 (18H), and a multiplet at 2.60$\delta$ (4H).

EXAMPLE XVIII

Preparation of 1,3,3,4,5,6,7- and 1,3,3,4,5,6,8-Heptamethylbicyclo-[2.2.2]-oct-5-en-2-one A two-liter autoclave is charged with 300 g of 93.7 percent pure 2,3,4,5,6,6-hexamethylcyclohexa-2,4-dienone, pressurized to 75 psig with propylene, and heated. The pressure gradually rises to about 530 psig at 200°–220°C, where the pressure begins to decrease and the temperature rises more rapidly. At this juncture the temperature is controlled in the range of 210°–215°C.

After one hour at this controlled temperature range, the mixture is cooled and held overnight. The contents of the autoclave are discharged and distilled in a 9-inch Goodloe column at 103°–105°C and 1.3–1.8 mm Hg to provide 360.5 g of a mixture of Compounds (XXIX) and (XXX).

Mass spectral data show m/e peaks at 150, 135, 220 (molecular), 41, 119, and 178.

This material has patchouli aroma nuances.

EXAMPLE XIX

Preparation of
1,2,3,3,4,5,6,7-Octamethyl-[2.2.2]-bicyclo-oct-5-en-2-ol and
1,2,3,3,4,5,6,8-Octamethyl-[2.2.2]-bicyclo-oct-5-en-2-ol A dry 250 ml three-necked flask purged with nitrogen and equipped with stirrer and reflux condenser is charged with 26 ml of a solution of 2 molar methyl magnesium chloride in tetrahydrofuran. During five minutes a mixture of 25 ml tetrahydrofuran and 8.0 g of 1,3,3,4,5,6,7-heptamethyl-[2.2.2]-bicyclo-oct-5-en-2-one and 1,3,3,4,5,6,8-octamethyl-[2.2.2]-bicyclo-oct-5-en-2-one is added. The reaction mass is then stirred at reflux after completion of the addition and is monitored by GLC analysis.

After 17 hours, only a trace of starting material remains. The mixture is then cooled to 10°C and hydrolyzed using saturated ammonium chloride solution. The reaction mass is then filtered and stripped on low vacuum.

The 7.9 g of product is analyzed by mass spectral techniques and is found to be a mixture of Compounds (XXXI) and (XXXII), the mass spectral analysis showing m/e peaks at 150, 135, 41, 43, 119, and 236 (molecular).

The material has a camphoraceous odor.

EXAMPLE XX

Preparation of
1,3,3,4,5,6,7-Heptamethyl-[2.2.2]-bicyclo-oct-5-en-2-ol and
1,3,3,4,5,6,8-Heptamethyl-[2.2.2]-bicyclo-oct-5-en-2-ol A dry 250 ml three-necked flask fitted with stirrer, thermometer, reflux condenser, dropping funnel and nitrogen bubbler is charged with 35 ml of anhydrous diethyl ether and 1.5 g of lithium aluminum hydride, and the mixture is heated to reflux with stirring. Once at reflux, heating is discontinued and a mixture of 10 g of 1,3,3,4,5,6,7-heptamethyl-[2.2.2]-bicyclo-oct-5-en-2-one and 1,3,3,4,5,6,8-heptamethyl-[2.2.2]-bicyclo-oct-5-en-2-one and 20 ml of anhydrous diethyl ether is added dropwise over 14 minutes so as to maintain reflux.

After completion of the addition, the mixture is stirred for 75 minutes at reflux. A GLC sample after that time shows three new peaks and little starting material remaining. The mixture is allowed to stand overnight and 15 ml of water is added dropwise with cooling. The reaction mixture is filtered and the filtrate is dried over anhydrous magnesium sulfate and stripped of solvent.

The residue weighing 10.1 g shows 5 to 6 percent starting material. Three new peaks are in the ratio of 24, 29, 40, and 8.1 g of the residue is distilled obtaining a yield of 6.7 of 1,3,3,4,5,6,7-heptamethyl-[2.2.2]-bicyclo-oct-5-en-2-ol and 1,3,3,4,5,6,8-heptamethyl-[2.2.2]-bicyclo-oct-5-en-2-ol.

Mass spectral analysis shows m/e peaks at 135, 150, 41, 119, 91, 43, and 222 (molecular).

The material has a warm, woody odor.

EXAMPLE XXI

Preparation of 1,2,3,3,4,5,6-Heptamethylbicyclo-[2.2.2]-oct-5-en-2-ol

A 12-liter flask fitted with a stirrer, thermometer, condenser, and Bidwell trap is charged with 792 g of 1,3,3,4,5,6-hexamethylbicyclo-[2.2.2]-oct-5-en-2-one, 2000 ml of 3M methyl magnesium chloride in tetrahydrofuran, and 2100 ml of toluene under a dry nitrogen atmosphere, and the contents are heated to reflux (about 65°-70°C). The tetrahydrofuran is removed during 50 minutes as the temperature gradually rises to 95°C. Thereafter the temperature is allowed to rise to 100°C and held there for 1.5 hours.

The mixture is cooled to 30°C, 400 ml of saturated aqueous ammonium chloride is added with cooling to maintain the temperature below 35°C, the mixture is filtered, the filtrate is washed with two one-liter portions of diethyl ether, and the combined organic layers are stripped (distilled) to provide 893 g of crude product. The crude material is rush-distilled through a 12-inch stone saddle-packed column.

The material boiling at 143°-192°C at 0.3-0.4 mm Hg is redistilled through a 12-inch Goodloe column to obtain 669 g of Compounds (IIa) and (IIb).

Compound (XXXIII) is similarly prepared by reacting 1,3,3-trimethylbicyclo-[2.2.2]-oct-5-en-2-one with n-butyl magnesium chloride. This material has a green, woody, camphoraceous aroma.

EXAMPLE XXII

Tobacco

A tobacco flavoring formulation is prepared by admixing the following materials:

| Ingredient | Amount (parts) |
|---|---|
| Ethyl butyrate | 0.05 |
| Ethyl valerate | 0.05 |
| Maltol | 2.00 |
| Commercial cocoa extract | 26.00 |
| Commerical coffee extract | 10.00 |
| 95% aqueous ethanol | 20.00 |
| Water | 41.90 |

The flavoring formulation is added to smoking tobaccos (bright, burley, Turkish, homogenized tobacco and stems) at the rate of 0.5–3 percent by weight of the tobacco. The tobacco is then formulated into cigarettes by the usual manufacturing procedures. At the rate of 10 ppm, to each cigarette is added 1,2,3,3,4,5,6-heptamethyl bicyclo-[2.2.2]-oct-5-en-2-ol.

The use of this material imparts to the overall flavor of the tobacco in the cigarettes, an excellent spicy balsamic green rich note and gives the tobacco in the cigarettes more body and causes it to be sweeter in taste.

EXAMPLE XXIII

Walnut Flavor

A walnut flavor material is prepared by admixing the following materials:

| Ingredient | Amount (parts) |
|---|---|
| Ethyl-2-methylbutyrate | 10.0 |
| Vanillin | 40.0 |
| Butyl valerate | 40.0 |
| 2,3-Diethylpyrazine | 5.0 |
| 2-Hydroxy-3-methyl-2-cyclopentene-1-one | 80.0 |
| Benzaldehyde | 60.0 |
| Valerian oil India (1% in 95% aqueous ethanol) | 0.5 |

| Ingredient | Amount (parts) |
| --- | --- |
| Propylene glycol | 764.5 |

A second identical flavor is made up except that 1,2,3,3,4,5,6-heptamethylbicyclo-[2.2.2]-oct-5-en-2-ol is added at the rate of 0.05 percent thereto.

Both flavors are compared in water at the rate of 20 ppm.

The flavor containing the 1,2,3,3,4,5,6-heptamethyl-bicyclo-[2.2.2]-oct-5-en-2-ol produces a rich, characteristic, black walnut taste, having the desired notes of dry black walnut. The flavor without this material is harsher and more chemical in taste and lacking certain desired nuances present in the natural dry black walnut flavor.

EXAMPLE XXIV

To a standard vending machine cola beverage, 1,2,3,3,4,5,6-heptamethylbicyclo-[2.2.2]-oct-5-en-2-ol is added at the rate of 0.02 ppm. As a result of the addition of this compound at the given rate, the beverage has a balsamic, woody, earthy, topnote and taste contributing to a fuller richer mouthfeel. This is the same effect that is achieved by adding natural patchouli oil to the beverage.

EXAMPLE XXV

Perfume

The following perfume base formulation is prepared:

| Ingredient | Amount (parts) |
| --- | --- |
| α-Ethylcrotonic acid | 1 |
| Vanillin | 20 |
| Labdanum resin absolute 50% (in ethyl alcohol 95%) | 50 |
| Cinnamic alcohol | 50 |
| Mixture of ortho- and para-methyl-phenyl-ethyl alcohol | 50 |
| Benzoin | 100 |
| 1,3,3,4,5,6-Hexamethylbicyclo-[2.2.2]-oct-5-en-2-one | 10 |
| 1,3,3,5,Tetramethyl-7-carbomethoxy-bicyclo-[2.2.2]-oct-5-ene | 20 |

The 1,3,3,4,5,6-hexamethylbicyclo-[2.2.2]-oct-5-en-2-one imparts a warm, woody fruity note to the overall amber aroma of the above formulation. The 1,3,3,5-tetramethyl-7-carbomethoxy-bicyclo-[2.2.2]-oct-5-ene imparts a warm, woody fruity note which is modified by a green figgy safral tone which helps round out the amber aroma.

EXAMPLE XXVI

The following honey perfume base formulation is prepared:

| Ingredient | Amount (parts) |
| --- | --- |
| 1,3,3,5-Tetramethyl-7 and 8-cyanobicyclo-[2.2.2]-octane | 100 |
| 1,3,3,5-Tetramethyl-7 and 8-acetylbicyclo-[2.2.2]-oct-5-ene | 150 |
| Phenylacetic acid | 100 |
| Coumarin | 100 |
| Benzyl benzoate | 400 |
| Phenylethylphenyl acetate | 100 |
| Phenylethyl alcohol | 100 |
| Dimethylbenzlcabinyl acetate | 10 |
| Phenylacetaldehyde dimethyl acetal | 1 |

| Ingredient | Amount (parts) |
| --- | --- |
| Methyl anthranilate | 10 |

The 1,3,3,5-tetramethyl-7 and 8-cyanobicyclo[2.2.2]-octane imparts to the honey perfume formulation, a woody, minty note considered to be necessary for the natural honey character thereof. The 1,3,3,5-tetramethyl-7 and 8-acetylbicyclo-[2.2.2]-oct-5-ene imparts to this honey formulation, a fruity slightly camphoraceous note which is also considered to be necessary for the natural honey character of this aroma.

EXAMPLE XXVII

The following geranium bourbon perfume formulation is prepared:

| Ingredient | Amount (parts) |
| --- | --- |
| Benzyl butyrate | 5 |
| Bois de rose | 10 |
| Citronelly formate | 35 |
| Citronellyl Acetate | 15 |
| Geranyl Acetate | 40 |
| Geranoil | 225 |
| Citronellol | 350 |
| Dimethylbenzyl varbinyl acetate | 4 |
| 5- and 6-Isopropyl-1,2,3-tri-methylbicyclo-[2.2.2]-octa-5,7-dien-2-one | 20 |
| 2-(1 and 4)-isopropyl-4-(and 1)-methyl-bicyclo-[2.2.2]-oct-2-en-5-yl-1,3-dioxlane | 15 |

The 5- and 6-Isopropyl-1,3,3-trimethylbicyclo-[2.2.2]-octa-5,7-dien-2-one imparts a minty, woody peppery nuance and the 2-(1 and 4)-isopropyl-4-(and 1)-methyl-bicyclo-[2.2.2]-oct-2-en-5-yl-1,3-dioxolane imparts a rosey, rhodinol, peppery, woody dry-out necessary for the geranium character of this geranium bourbon formulation.

EXAMPLE XXVIII

The following floral perfume mixture is prepared:

| Ingredient | Amount (parts) |
| --- | --- |
| 1,2,3,3,4,5,6-Heptamethylbicyclo-[2.2.2]-oct-5-en-2-ol | 40 |
| Bergamot oil Italian | 150 |
| Orange oil Florida | 100 |
| Lemon oil California | 30 |
| Gamma methyl ionone coeur | 30 |
| Eugenol | 10 |
| 4-(4-Hydroxy-4-methylpentyl)-3-cyclohexene-1-carboxaldehyde | 30 |
| Styrallyl acetate | 5 |
| Ylang extra | 25 |
| Petitgrain oil | |
| Chamomile oil | 1 |

The 1,2,3,3,4,5,6-heptamethylbicyclo-[2.2.2]-oct-5-en-2-ol imparts a patchouli effect to this floral perfume composition.

EXAMPLE XXIX

A total of 100 grams of soap chips are mixed with one gram of the perfume mixture prepared according to Example XXV until a substantially homogeneous composition is obtained. After milling and forming into soap bars the soap composition manifests a characteristic amber aroma with warm woody fruity notes imparted thereto.

EXAMPLE XXX

"Honey" Cologne

The following cologne is prepared:

| Ingredient | Amount (parts) |
|---|---|
| Perfume formulation of Example XXVI | 15 |
| Bergamot oil | 8 |
| Lavender oil | 1 |
| Clove oil | 1 |
| Nutmeg oil | 1.5 |
| Coriander oil | 1 |
| Sandalwood oil | 3.5 |
| Benzoin | 5 |
| Musk extract | (3% in diethyl phthalate) |
| Rose water triple | 100 |
| Orange flower water triple | 100 |
| Ethyl alcohol (95%) | 800 |

The resulting eau de cologne has an aroma substantially identical to that of the classical "aqua mellis".

EXAMPLE XXXI

A total of 100 grams of a detergent is mixed with 0.15 grams of the perfume mixture of Example XXVII until a substantially homogeneous composition is obtained. The resulting composition manifests a characteristic geranium bourbon aroma having minty, woody, peppery nuances giving rise to a detergent composition having a pleasant geranium bourbon note.

It will be understood from the present disclosure that the various materials contemplated herein are also useful as intermediates for fragrance and flavor materials and for the preparation of other compounds.

What is claimed is:

1. A process for treating a tobacco which comprises adding thereto a small but effective amount of 1,2,3,3,4,5,6-heptamethyl bicyclo-[2.2.2]-oct-5-en-2-ol to alter the organoleptic properties of the tobacco.

2. A tobacco product comprising tobacco and an organoleptic altering amount of 1,2,3,3,4,5,6-heptamethyl bicyclo-[2.2.2]-oct-5-en-2-ol.

* * * * *

UNITED STATES PATENT AND TRADEMARK OFFICE
CERTIFICATE OF CORRECTION

PATENT NO. : 3,967,629
DATED : July 6, 1976
INVENTOR(S) : ROBERT L. CHAPPELL, EDWARD J. SHUSTER, JOAQUIN F. VINALS, and MANFRED H. VOCK It is certified that error appears in the above-identified patent and that said Letters Patent are hereby corrected as shown below:

Col. 19, line 61, correct the spelling of "about"

Col. 31, Example XXVI, under "Ingredient", "Dimethyl-benzylcabinyl" should read --Dimethylbenzyl-carbinyl--

Col. 32, Example XXVII, under "Ingredient", after "Dimethylbenzyl" change "varbinyl" to --carbinyl--

Signed and Sealed this

Twenty-third Day of November 1976

[SEAL]

Attest:

RUTH C. MASON
Attesting Officer

C. MARSHALL DANN
Commissioner of Patents and Trademarks